US00PP13000P2

(12) United States Plant Patent
Armitage

(10) Patent No.: US PP13,000 P2
(45) Date of Patent: Sep. 24, 2002

(54) SCABIOUS PLANT 'LEMON SORBET'

(75) Inventor: Allan M. Armitage, Athens, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 09/515,977

(22) Filed: Feb. 28, 2000

(51) Int. Cl.[7] ..... A01H 5/00
(52) U.S. Cl. ..... Plt./263

(58) Field of Search ..... Plt./263

*Primary Examiner*—Kent L. Bell
(74) *Attorney, Agent, or Firm*—Needle & Rosenberg, P.C.

(57) ABSTRACT

A new and distinct plant of *Scabiosa ochroleuca* named 'Lemon Sorbet' was selected as a chance seedling in The University of Georgia Horticulture Trial Gardens in Athens, Ga., USA. The new cultivar is distinguished by the unique combination of dwarf habit and primrose yellow flowers. The cultivar demonstrates good disease tolerance and is well-suited for ornamental use.

2 Drawing Sheets

SUMMARY OF THE INVENTION

The present invention comprises a new and distinct plant of *Scabiosa ochroleuca,* which has been given the name 'Lemon Sorbet'. The following traits have been repeatedly observed and are the most pronounced characteristics of this new cultivar when grown in Georgia, and in combination, they distinguish it from existing cultivars known to the inventor.

1. Dwarf habit
2. Primrose Yellow flower color

DETAILED DESCRIPTION

Background of the Invention

Figure 1:
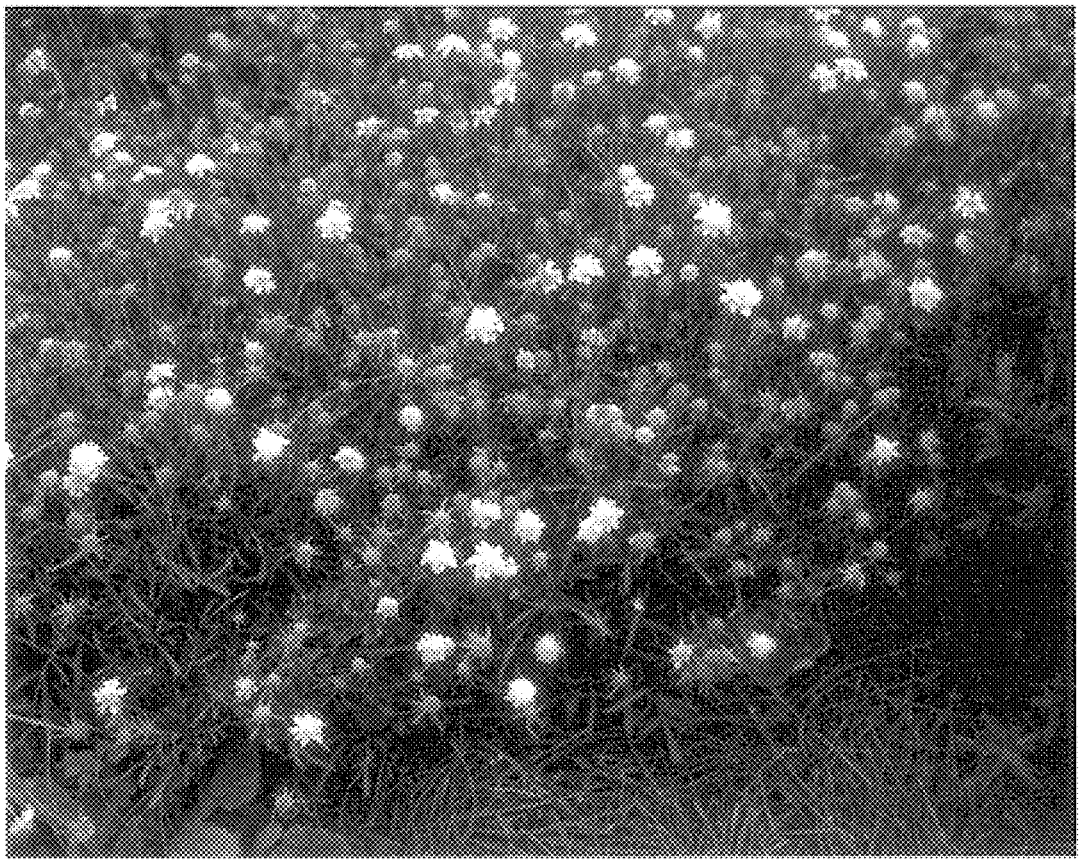
FIG. 1 shows the typical habit of a typical flowering mature plant of Scabiosa 'Lemon Sorbet'.
Figure 2:
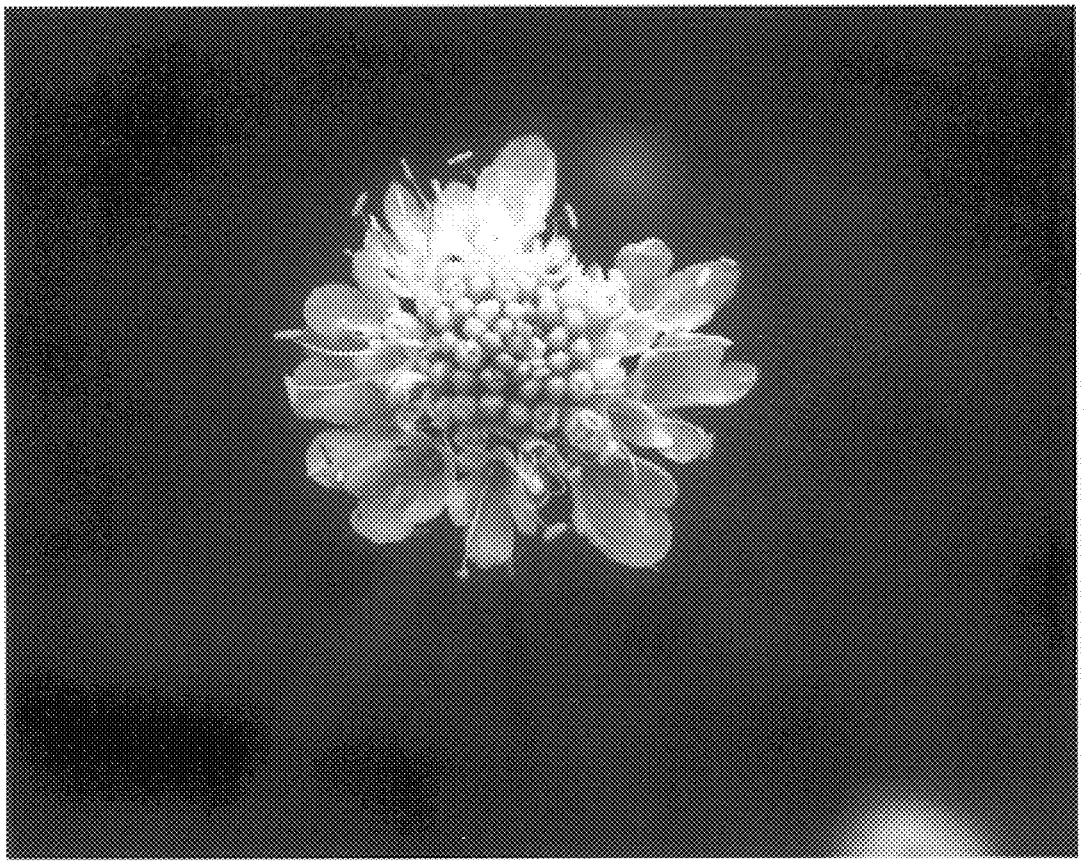
FIG. 2 shows the shape and color of a typical inflorescence of Scabiosa 'Lemon Sorbet'.

Scabious, a common name for the botanical genus Scabiosa, is a well known genus in ornamental horticulture. Well over 95% of scabious sold in the United States have blue flowers. Lavender and pink cultivars have also been developed, including the cultivar 'Pink Mist' described in U.S. Plant Pat. No. 8,957, and the non- patented cultivars 'Butterfly Blue' and 'Fama'.

Origin of the Invention

The plant was first noticed in the perennial bed in the University of Georgia garden, at Athens, Clarke County, Ga., USA. It was a chance seedling found among other scabious grown in the garden. It was first noticed in 1995 and evaluated at that time, then routinely evaluated since that time.

Methods of Reproduction

Asexual reproduction of 'Lemon Sorbet' has been successfully accomplished by simple division of plant clumps. Asexual reproduction by tissue culturing, using leaves as explants is also possible. Asexual reproduction demonstrates that the unique features of 'Lemon Sorbet' are stable and are reproduced true-to-type in subsequent generations.

General Botanical Description

This plant is a herbaceous perennial species with a rosette of basal foliage, that typically grows about 8–15" tall at maturity in Georgia. It is distinguished from other scabious known to the inventor by having light yellow flowers and a dwarf habit. The following description defines the overall appearance of one year old plants as grown under normal conditions in The University of Georgia Horticulture Trial Gardens in Athens, Ga., U.S.A, that is: summers are hot and humid with average daytime temperatures between 50–110° F. (average: 90° F.), and winters that are rainy, with average temperatures around 40° F.

Stems: The plants have rounded stems, about 10" in length, above which is the peduncle, the flower stem. The intermode length averages 1.1 cm and the color is RHS 138B.

Leaves: Basal leaves are obovate and measure approximately 3–4" long and 1–2" wide. The basal leaves are petiolate (petiole approximately 1" long) with crenate margins. The colors of the upper and lower surfaces of the basal leaves are RHS 137A and RHS 138B, respectively. Stem leaves, which arise from the axis on which the flower buds appear, are pinnatifid, with one linear terminal lobe with acuminate apex (3–6 cm) and 3 to 4 pinnately arranged side lobes with acuminate apex (2–4 cm). Leaves are arranged oppositely with pubescence on top and under sides. Stem leaf color is RHS 137B on the upper surface and RHS 137C on the lower surface. Table 1 presents a comparison of leaf and inflorescence measurements among 'Lemon Sorbet' and other scabious.

TABLE 1

Average leaf size, inflorescence characteristics and height for selected Scabious Cultivars

| | Leaf Size | | | |
|---|---|---|---|---|
| | Basal Leaf | Stem Leaf | Color | Diameter |
| 'Lemon Sorbet' | 4"× 2" | 3" × 1" | 1C upper surface<br>ID lower surface | 1" |
| 'Butterfly Blue' | 6"× 2" | 5" × 1" | 90D | 2" |

TABLE 1-continued

Average leaf size, inflorescence characteristics and height for selected Scabious Cultivars

| | Leaf Size | | | |
|---|---|---|---|---|
| | Basal Leaf | Stem Leaf | Color | Diameter |
| 'Pink Mist' | 6"× 2" | 5" × 1" | 75A | 2" |
| 'Fama' | 6½"× 2" | 6" × 1½" | 90D | 3" |

Height:

*'Lemon sorbet'*.—8–15".

*'Butterfly blue'*.—18–24".

*'Pink mist'*.—18–24".

*'Fama'*.—24–36".

Inflorescence:

Flowers are borne singly in terminal heads, subtended by 1–2 series of involucral bracts. The peduncle averages 11.08 cms, with a 1 mm diameter and color RHS 138B. The involucral bracts are nine in number, averaging 88 mm in length and 20 mm wide. The color of the upper and lower surfaces is RHS 137C. They have one prominent midvein with an entire margin and acuminate apex.

The mature flower heads average 2.05 cm in diameter, containing approximately 50 flowers per inflorescence. The marginal flowers, approximately 15 in number, average 52 mm in diameter. The corolla has five unequal lobes which may be two-lipped, and a short tube. The flower has 4 stamens (5–6 mm in length) with 1 mm long anthers. The pistil is 3–4 mm long. The calyx is cup shaped with 5 bristly setae (2–3 mm long) enveloped by a cup shaped involucel. The inner flowers average 22.5 mm in diameter.

*Timing*.—Flowers are produced in early and mid spring, May–June in Athens, Ga. The one year old plants in the garden averaged 27 inflorescences per plant.

*Color*.—The flower head is RHS 1D. Table 1 provides a comparison of inflorescence color and size of 'Lemon Sorbet' with other scabious. The color of the upper flower surface is RHS 1C, the lower flower surface is RHS 1D, and the color of unopened buds is RHS 1B.

*Fragrance*.—None.

*Seed*.—Flowers are essentially sterile. No seeds were produced on the plants under the conditions of growth.

OTHER CHARACTERISTICS

The plants have been observed for about four years and no disease or insect susceptibility has been noted. In Georgia, typical insects include the three spotted spider mite and the Western flower thrips, while typical disease pathogens include powdery mildew and root rot pathogens. No particular susceptibility to these insects and diseases has been observed.

'Lemon Sorbet' has excellent cold hardiness, tolerating winter temperatures between −10 and −20 degrees F. (USDA zone 5).

What is claimed:

1. A new and distinct plant of *Scabiosa ochroleuca* as herein shown and described, that is characterized by a unique combination of dwarf habit and primrose yellow flowers.

* * * * *